McKenzie et al.

United States Patent [19]

[11] 4,431,661
[45] Feb. 14, 1984

[54] 5-ARYL-3-AZABICYCLO[3.2.0]HEPTAN-6-ONE ACETALS, AND ANALGESIC USE THEREFOR

[75] Inventors: Thomas C. McKenzie, Pearl River; Joseph W. Epstein, Monroe; William J. Fanshawe, Pearl River, all of N.Y.

[73] Assignee: American Cyanamid Company, Stamford, Conn.

[21] Appl. No.: 294,548

[22] Filed: Aug. 20, 1981

[51] Int. Cl.³ .................. C07D 209/02; C07D 405/02; A61K 31/40
[52] U.S. Cl. .................................... 424/274; 548/411; 548/452
[58] Field of Search ....................... 548/411, 407, 452; 424/274

[56] References Cited

U.S. PATENT DOCUMENTS 4,088,652 5/1978 Fanshawe et al. ................. 548/515
4,118,417 10/1978 Epstein ............................ 548/515 X
4,131,611 12/1978 Fanshawe et al. ................. 548/515

Primary Examiner—Paul M. Coughlan, Jr.
Assistant Examiner—D. B. Springer
Attorney, Agent, or Firm—Mary-Ellen M. Timbers

[57] ABSTRACT

Novel compounds are disclosed having the formula

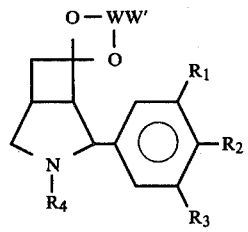

wherein $R_1$, $R_2$ and $R_3$ are each individually selected from the class consisting essentially of hydrogen, hydroxy, chloro, bromo, an alkyl radical having up to 3 carbon atoms, an alkoxy radical having up to 3 carbon atoms, and trifluoromethyl, and any two or more of $R_1$, $R_2$ and $R_3$ may be the same; $R_4$ is selected from the class consisting essentially of hydrogen, an alkyl radical having up to 3 carbon atoms, an allyl radical having up to 4 carbon atoms, the cyclopropylmethyl radical or the phenethyl radical; and W and W' each represent a monovalent alkyl moiety having up to 3 carbon atoms or W-W' jointly represent a divalent moiety of the formula

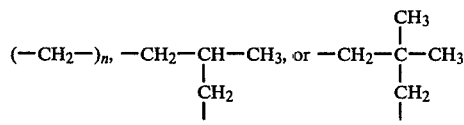

where n is an integer of 2 or 3, including individual optically active isomers, racemic mixtures thereof, and non-toxic pharmacologically-acceptable acid-addition salts thereof. Such compounds are useful as analgesics in mammals. They can be prepared by irradiating with ultra-violet light a mixture of a dialkoxyethylene and a maleimide of the formula

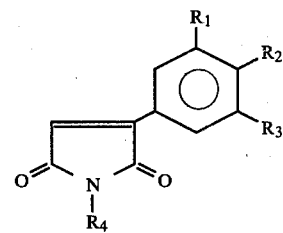

to produce a 4,4-dialkoxy-N-alkyl-1-phenyl-1,2-cyclobutanedicarboximide, and chemically reducing the same. Three other processes of preparation are also described.

24 Claims, No Drawings

5-ARYL-3-AZABICYCLO[3.2.0]HEPTAN-6-ONE ACETALS, AND ANALGESIC USE THEREFOR

FIELD OF THE INVENTION

This invention relates to novel compounds of the class of 5-aryl-3-azabicyclo[3.2.0]heptan-6-one acetals, and their acid-addition salts, to the use of such compounds as analgesics in mammals, and to processes for the preparation of such compounds.

BACKGROUND

The applicants are not aware of any prior art patents or publications which, in their respective judgment, should be deemed to anticipate the compounds and processes described and claimed herein. By way of background, U.S. Pat. Nos. 4,088,692, 4,118,417 and 4,131,611 are cited.

DESCRIPTION OF THE INVENTION

The acetal compounds of this invention include those of the class represented by formula (11)

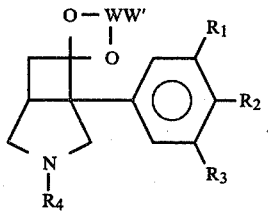
(11)

wherein $R_1$, $R_2$ and $R_3$ are each individually selected from the class consisting essentially of hydrogen, hydroxy, chloro, bromo, an alkyl radical having up to 3 carbon atoms, an alkoxy radical having up to 3 carbon atoms, and trifluoromethyl, and any two or more of $R_1$, $R_2$ and $R_3$ may be the same; $R_4$ is selected from the class consisting essentially of hydrogen, an alkyl radical having up to 3 carbon atoms, an 2-alken-1-yl radical having up to 4 carbon atoms, the cyclopropylmethyl radical or the phenethyl radical; and W and W' each represent a monovalent alkyl moiety having up to 3 carbon atoms or W-W' jointly represent a divalent moiety of the formula

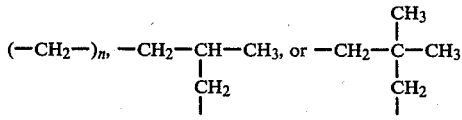

wherein n is an integer of 2 or 3; racemic mixtures thereof; and the non-toxic pharmacologically acceptable acid-addition salts thereof.

The various subscripts and symbols for chemical moieties, once defined herein, continue to have the same definition unless otherwise expressly stated.

The novel compounds of the present invention possess at least two asymmetric carbon atoms and thus can be produced as racemic mixtures or as individual optically active isomers. The racemic mixtures can be resolved if desired at appropriate stages by methods known to those skilled in the art, to obtain the respective individual isomers. It is to be understood that the racemic mixtures and the individual optically active isomers are encompassed within the scope of the subject matter claimed herein.

The free bases of the compounds of this invention are, in general, soluble in organic solvents such as methanol, ethanol, isopropyl alcohol, N,N-dimethylformamide, dimethyl sulfoxide, and the like. They form acid-addition salts with a variety of organic and inorganic salt-forming reagents. Thus, acid-addition salts, formed by admixture of the organic free base with an equivalent amount of an acid, suitably in a neutral solvent, are formed with such acids as hydrochloric, hydrobromic, phosphoric, sulfuric, citric, fumaric, acetic, ascorbic, and gluconic acid, and the like. These salts are generally soluble in water and in lower alkanols, such as methanol. For analgesic purposes, the organic free bases are equivalent to their non-toxic acid-addition salts.

Specific new 5-aryl-3-azabicyclo[3.2.0]heptan-6-one acetals of the present invention include:

3-Methyl-5-(m-chlorophenyl)-3-azabicyclo[3.2.0]heptan-6-one dimethyl acetal;

3-Methyl-5-(p-methylphenyl)-3-azabicyclo[3.2.0]heptan-6-one, dimethyl acetal;

3-Methyl-5-(3',4',5'-trimethoxyphenyl)-3-azabicyclo[3.2.0]heptan-6-one, dimethyl acetal;

3-Methyl-5-(p-methoxyphenyl)-3-azabicyclo[3.2.0]heptan-6-one, dimethyl acetal;

3-Methyl-5-(3',4'-dichlorophenyl)-3-azabicyclo[3.2.0]heptan-6-one, dimethyl acetal;

3-Methyl-5-(m-trifluoromethyl)-3-azabicyclo[3.2.0]heptan-6-one, dimethyl acetal;

3-Methyl-5-(m-methoxyphenyl)-3-azabicyclo[3.2.0]heptan-6-one, dimethyl acetal;

5-(m-Methoxyphenyl)-3-azabicyclo[3.2.0]heptan-6-one, dimethyl acetal;

3-Allyl-5-(m-methoxyphenyl)-3-azabicyclo[3.2.0]heptan-6-one, dimethyl acetal;

3-Cyclopropylmethyl-5-(m-methoxyphenyl)-3-azabicyclo[3.2.0]heptan-6-one, dimethyl acetal;

3-Phenethyl-5-(m-methoxyphenyl)-3-azabicyclo[3.2.0]heptan-6-one, dimethyl acetal;

3-Methyl-5-(m-hydroxyphenyl)-3-azabicyclo[3.2.0]heptan-6-one, dimethyl acetal;

3-Methyl-5-phenyl-3-azabicyclo[3.2.0]heptan-6-one, dimethyl acetal;

5-(m-Methoxyphenyl)-3,5',5'-trimethyl-spiro[3-azabicyclo[3.2.0]heptan-6,2'[1,3]dioxane];

3-Methyl-5-(m-methoxyphenyl)-spiro[3-azabicyclo[3.2.0]heptan-6,2'-[1,3]dioxolane]; and 3-Methyl-5-(p-chlorophenyl)-3-azabicyclo[3.2.0]heptan-6-one, dimethyl acetal.

Such compounds are useful in a method of treating pain in mammals, which method comprises administering to a mammal a therapeutically effective amount of a compound of formula (11), including racemic mixtures, optically-active isomers, non-toxic pharmacologically-acceptable acid-additions thereof, and mixtures of the foregoing. Preferred compounds are those in which one of $R_1$, $R_2$ or $R_3$ is alkoxy, especially methoxy, and the others are hydrogen; and those wherein $R_4$ is lower alkyl, especially methyl.

The novel 5-aryl-3-azabicyclo[3.2.0]heptan-6-one acetals (of formula (11)) of this invention may be prepared by several alternative processes. For example, they may be prepared by irradiating with ultra-violet light through pyrex-type glass a mixture of a dialkoxyethylene having the formula (12)

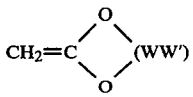

and a maleimide of the formula (13)

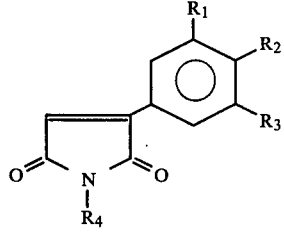

to produce a 4,4-dialkoxy-N-alkyl-1-phenyl-1,2-cyclobutanedicarboximide having the formula (14)

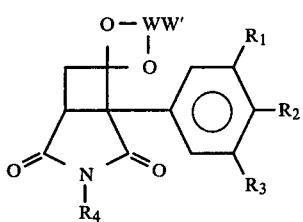

and thereafter chemically reducing said cyclobutanedicarboximide to a compound of formula (11). The reaction of a dialkoxyethylene of formula (12) and a maleimide of formula (13) may be conducted in the absence of a solvent, or in a cosolvent such as dichloromethane. The imide of formula (14) is chemically reduced with an anhydride reducing agent such as lithium aluminum hydride or sodium bis-(2-methoxyethoxy) aluminum hydride in an inert solvent such as tetrahydrofuran or toluene, at temperatures in the range of about 20° C. to about 100° C.

As a second alternative, the compounds of formula (11) may be prepared by the interaction of a ketone of the formula (15)

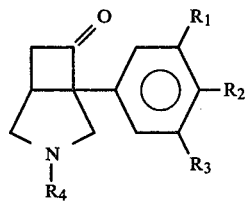

with a straight- or branched-chain alkanol having 1 to 4 carbon atoms or a straight- or branched-chain glycol having 2 to 5 carbon atoms, in the presence of a strong acid. Methanol or ethylene glycol are preferred, but other alkanols, such as ethanol or 1-propanol, may be employed, as well as other glycols such as propylene glycol, tetramethylene glycol or diethylene glycol. The strong acid may be any of the three mineral acids (hydrochloric, sulfuric or nitric acid) or a strong organic acid, such as paratoluene sulfonic acid (which is preferred), benzene sulfonic acid or methane sulfonic acid.

Ketones of formula (15) may be prepared by the hydrolysis of a 5-aryl-3-azabicyclo[3.2.0]heptan-6-one acetal of this invention, with an acid such as hydrochloric acid.

The ketones of formula (15) may also be prepared by the reduction of a dichloroketone having the formula (16)

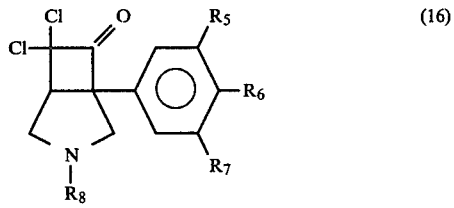

wherein $R_5$, $R_6$ and $R_7$ are defined the same as $R_1$, $R_2$ and $R_3$, except excluding any hydroxyl radical, and wherein $R_8$ is the same as $R_4$, except excluding hydrogen or an alken-1-yl radical, with zinc and acetic acid. A related process is described by P. Crabbe, et al., *Bull. Soc. Chim. Belg.*, Vol. 86, page 109 (1977). Chloroketones of formula (16) may be prepared by the interaction of pyrrolines of formula (17)

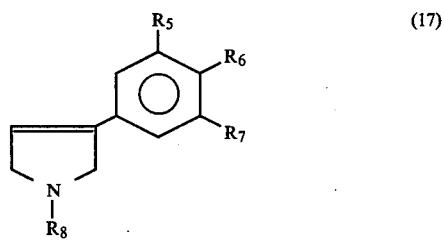

with dichloroketene. A related process is described by L. Krepski and A. Hassner, *J. Org. Chem.*, Vol. 43, page 2879 (1978).

As a third alternative, those novel 5-aryl-3-azabicyclo[3.2.0]heptan-6-one acetals of this invention which have the structure of formula (18)

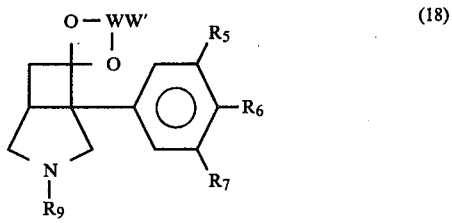

wherein $R_9$ is defined the same as $R_4$ but excluding hydrogen, may be prepared by the reaction of an alkylating agent with a compound of formula (19)

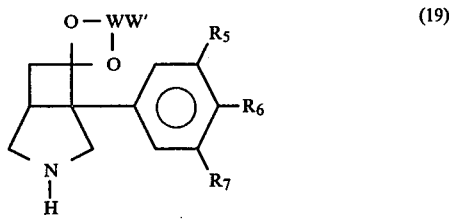

The alkylating agent may be a $C_1$-$C_6$ lower alkyl, allyl, or cyclopropylmethyl halide, sulfate, or methanesulfonate, such as methyl iodide, allyl bromide, or cyclopropylmethyl bromide. The reaction is preferably conducted in a solvent such as a lower alkanol (e.g., ethanol or isopropanol) or a lower ($C_6$-$C_8$) aromatic hydrocarbon (e.g., toluene or mixed xylenes), and in the presence of a base, such as sodium carbonate, which serves as an acid scavenger, at a temperature in the range of about 60° C. to 120° C.

As a fourth alternative, those novel 5-aryl-3-azabicyclo[3.2.0]heptan-6-one acetals of this invention which have the structure of formula (20)

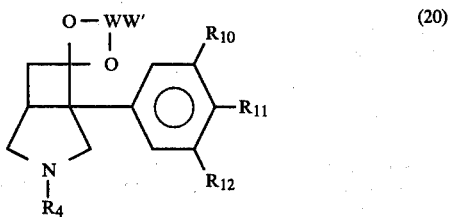

wherein $R_{10}$, $R_{11}$ and $R_{12}$ are selected from the class consisting essentially of hydrogen and hydroxyl and only one of $R_{10}$, $R_{11}$ and $R_{12}$ is hydroxyl, may be prepared by the reaction of a lower alkali metal lower alkyl mercaptide with a compound having the formula (21)

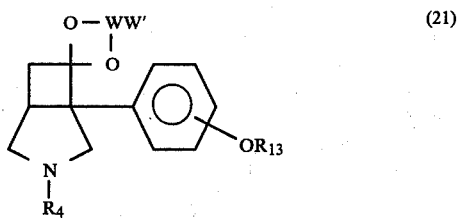

wherein $R_{13}$ is a $C_1$-$C_3$ lower alkyl, preferably methyl, at the para- or a meta-position. The lower alkali metal is preferably sodium, but may also be potassium or lithium. The lower alkyl moiety of the mercaptide has 1 to 3 carbon atoms, such as methyl, ethyl or isopropyl. The process is conducted in an unreactive polar solvent, preferably dimethylformamide. A related process is described by R. N. Mirrington and G. I. Feutrill, in *Org. Synth.*, Vol. 53, page 90 (John Wiley and Sons, New York, N.Y., 1973).

The compounds of the present invention exhibit analgesic activity when measured by a modification of the method of D. C. Atkinson and A. Cowan, J. Pharm. Pharmacol., Vol. 26, page 727 (1974).

In accordance with such test, male albino Wistar-strain rats from Royalhart farms, weighing 120-150 g. each, were deprived of food for about 20 hours. A 40% suspension of brewers' yeast in physiological saline was injected, at a volume of 0.25 ml. per rat, into the plantar surface of the left hind paw of each rat. Three hours later, at which time inflammation of the injected paw had developed, and prior to the administration of any therapeutic composition, an assessment was made of the walking gait of each rat, according to the following scoring system:

0—Normal gait in the presence of a severely inflamed paw. There is continuous use of the foot pad.
0.5—As above with intermittent mild limping.
1.0—Constant limping, but continuous use of the foot pad.
1.5—Limping with occasional three-legged gait (paw kept off walking surface) or intermittent use of digits in combination with foot pad.
2.0—Continuous three-legged gait and/or only the tips of the digits touch the walking surface. There is no use of the foot pad.

More than 95% of such rats exhibited a gait score of 2 before being given a test compound. The test compounds were dissolved or suspended in a suitable vehicle and administered orally by gavage or intraperitoneally at a dose of 25 mg./kg. of body weight in a volume of 0.5 ml. per 100 g. of body weight. Forty-five or 90 minutes later a post-administration assessment of walking gait was made as described above. A compound was considered to be active (i.e., to show analgesic activity) when there was at least a 50% reversal of the abnormal gait.

The results of this test when employing several compounds of this invention are given in Table I.

TABLE I

| Compound | Result |
| --- | --- |
| 3-Methyl-5-phenyl-3-azabicyclo[3.2.0]heptan-6-one, dimethyl acetal, fumarate | Active |
| 3-Methyl-5-(m-methoxyphenyl)-3-azabicyclo[3.2.0]heptan-6-one, dimethyl acetal, fumarate | Active |
| 3-Allyl-5-(m-methoxyphenyl)-3-azabicyclo[3.2.0]heptan-6-one, dimethyl acetal | Active |
| 5-(m-Methoxyphenyl)-3-azabicyclo[3.2.0]heptan-6-one, dimethyl acetal, fumarate | Active |
| 3-Methyl-5-(m-hydroxyphenyl)-3-azabicyclo[3.2.0]heptan-6-one, dimethyl acetal | Active |
| 5-(m-Methoxyphenyl)-3,5,5'-trimethyl-spiro[3-azabicyclo[3.2.0]heptan-6,2'-[1,3]dioxane] fumarate | Active |

Another test used to measured analgesic activity comprises an adaptation of the methods of G. Wolfe and A. D. MacDonald, J. Pharmacol., Exptl. Therap., Vol. 80, pages 300-307 (1944), and N. E. Eddy, et al., J. Pharmacol. Exptl. Therap., Vol. 98, pages 121-137 (1950). Individual mice were confined on a heated surface maintained at 55.0°±0.5° C. and the time required to elicit a response (licking of paws or an attempt to jump from the heated surface) was recorded. A maximum (cut-off) time of 30 seconds was used. Test compounds were prepared in a 2% starch vehicle containing 5% polyethylene glycol and one drop of Polysorbate 80 and administrated orally or subcutaneously at a dose of 20 mg./kg. of body weight in a constant volume of 10 ml./kg. of body weight. The criterion for analgesia is a 100% increase in response time over that of control mice treated with the vehicle alone. A representative compound of this invention, 3-methyl-5-(m-methoxyphenyl)-3-azabicyclo[3.2.0]heptan-6-one, dimethyl acetal, fumarate, is active when tested by this procedure.

Another procedure which indicates an analgesic mode of action comprises a modification of the method of W. D. Gray, et al., J. Pharmacol. Exptl. Therap., Vol. 172, pages 154-162 (1970), which in turn was based on the method of F. E. D'Amour and D. L. Smith, J. Pharmacol. Exptl. Therap., Vol. 72, pages 74-79 (1941). The tail of individual rats was exposed to a high intensity radiant heat stimulus 90 minutes after oral or intraperitoneal administration of the test compounds. The time required to elicit a threshold response (characteristic tail flick) was recorded. A maximum exposure (cut-off) time of 15 seconds was employed for the high-intensity stimulus. The test compounds were prepared in a 2% starch vehicle containing 5% polyethylene glycol and one drop of Polysorbate 80, and administered in a constant volume of 5 ml./kg. of body weight, either intraperitoneally at a dose of 25 mg./kg. of body weight or orally at multiple dose levels. The criterion for analgesia was a 100% increase in response time over that of control rats treated with the vehicle alone. The results of this test on representative compounds of this invention appear in Table II.

TABLE II

| Compound | Result |
| --- | --- |
| 3-Methyl-5-(m-methoxyphenyl)-3-azabicyclo-[3.2.0]heptan-6-one, dimethyl acetal, fumarate | Active |
| 3-Allyl-5-(m-methoxyphenyl)-3-azabicyclo-[3.2.0]heptan-6-one, dimethyl acetal | Active |

The active compounds of the present invention are effective analgesic agents in warm-blooded animals when administered in amounts ranging from about 5 mg. of about 200 mg. per kilogram of body weight per day. A preferred dosage regimen for optimum results would be form about 5 mg. to about 50 mg. per kilogram of body weight per day, and such dosage units are employed that a total of from about 350 mg. to about 3.5 g. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen or cherry flavoring. When the dosage unit form is a capsule, it may contain, a liquid carrier in addition to materials referred to above. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl-and propyl-parabens as preservatives, and a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

The active compounds of this invention may also be administered parenterally or intraperitoneally. Solutions or suspensions of these active compounds as a free base or a pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, a polyol (e.g., glycerol, propylene glycol or a liquid polyethylene glycol), suitable mixtures thereof, and vegetable oils.

EXAMPLE 1

3-Methyl-5-phenyl-3-azabicyclo[3.2.0]heptan-6-one, dimethyl acetal free base and fumarate salt A mixture of 1.0 g. of N-methyl-2-phenylmaleimide, (J. Org. Chem., Vol. 28, page 1713 (1963)), 10.0 g. of 1,1-dimethoxy-ethylene and a small portion of potassium carbonate was sealed in a Pyrex test tube. The tube was taped to the side of a water-jacketed Pyrex well and irradiated for 1½ hours with a 450 watt medium pressure mercury lamp. Cooling and filtration gave 1.36 g. of 1-phenyl-N-methyl-4-oxo-1,2-cyclobutanedicarboximide-4-dimethyl acetal as a white solid.

A mixture of 0.86 g. of the above compound and 10 ml. of Vitride (Reg. T.M.) [sodium bis(2-methoxyethoxy)aluminum hydride] was heated at reflux for 16 hours. The reaction mixture was cooled, carefully quenched with 10 N sodium hydroxide, diluted with water and extracted three times with ether. The combined extracts were washed with water, then with brine and then dried with sodium sulfate and evaporated, giving 0.66 g. of the desired base product as a yellow oil, IR(KBr) 2940 $(CH_2)$, 2776, $(NCH_3)$ cm$^{-1}$; $^1$H NMR $(CDCl_3)$ $\delta$ 7.27 (s, 5H, aromatic), 3.28 and 2.83 (s, 3H, $OCH_3$), 2.36 (s, 3H, $NCH_3$); (70 eV) m/e 247 (1.5%, M+), 159 (61.5, M—$CH_2C(OCH_3)_2$).

A 0.59 g. portion of this oil was dissolved in 2 ml. of hot acetone and this solution was added to a solution of 290 mg. of fumaric acid in 30 ml. of boiling acetone. Cooling and filtration gave 700 mg. of the desired fumarate salt as a white solid, m.p. 167°–169° C. Calculated for $C_{15}H_{21}NO_2 \cdot C_4H_4O_4$: C, 62.80; H, 6.93; N, 3.85. Found: C, 62.40; H, 7.10 and N, 3.70.

EXAMPLES 2-4

Following the procedure of Example 1, the imides named in the following Table III (Examples 2-4) were prepared, and converted to the corresponding 1-aryl-3-azabicyclo[3.2.0]heptan-6-one acetal fumarates, if desired.

A mixture of 5.0 g. of this carboximide, 50 ml. of Vitride (Reg. TM) and 50 ml. of toluene was stirred for ½ hour and then refluxed overnight. The reaction mixture was cooled, then carefully quenched with 36 ml. of 10 N sodium hydroxide and extracted with ether. The resulting red oil was subjected to Kugelrohr distillation at 145° C., 0.04 mm., giving 3.50 g. of the desired free

TABLE III

| Example | Imide | 5-Aryl-3-azabicyclo[3.2.0]heptan-6-one, acetal |
|---|---|---|
| 2 | N—Methyl-1-(m-chlorophenyl)-4-oxo-1,2-cyclobutanedicarboximide, dimethyl acetal | 3-Methyl-5-(p-chlorophenyl)-3-azabicyclo[3.2.0]-heptan-6-one, dimethyl acetal, fumarate, m.p. 170–172° C. $^1$H NMR (d$_6$DMSO) δ 7.29 (s, aromatic), 3.21 and 2.76 (s, OCH$_3$) |
| 3 | N—Methyl-1-(p-methylphenyl)-4-oxo-1,2-cyclobutanedicarboximide, dimethyl acetal, m.p. 138–144° C. | 3-Methyl-5-(p-methylphenyl)-3-azabicyclo[3.2.0]-heptan-6-one, dimethyl acetal, fumarate, m.p. 177–178° C. Calc. for C$_{16}$H$_{23}$NO$_2$.C$_4$H$_4$O$_4$: C, 63.64; H, 7.21; N, 3.71. Found: C, 63.66; H, 7.10, N, 3.45. $^1$H NMR (CDCl$_3$) δ 7.10 (s, 4H, aromatic), 3.20 and 2.70 (s, 3H, OCH$_3$), 2.56 (s, 3H, NCH$_3$) |
| 4 | N—Methyl-1-(3,4,5-trimethoxyphenyl)-4-oxo-1,2-cyclobutanedicarboximide, dimethyl acetal, m.p. 103–108° C. | 3-Methyl-5-(3',4',5'-trimethoxyphenyl)-3-azabicyclo[3.2.0]heptan-6-one, dimethyl acetal, m.p. 100–105° C. Calc. for C$_{18}$H$_{27}$NO$_5$: C, 64.07; H, 8.06; N, 4.15. Found: C, 64.01; H, 8.03; N, 4.09. $^1$H NMR (CDCl$_3$) δ 6.48 (s, 2H, aromatic), 3.90 (s, 9H, aromatic OCH$_3$), 3.32 and 2.88 (s, 3H, OCH$_3$), 2.42 (s, 3H, NCH$_3$) |

In the same manner, 3-methyl-5-(m-chlorophenyl)-3-azabicyclo[3.2.0]heptan-6-one, dimethyl acetal can be prepared from N-methyl-1-(m-chlorophenyl)-4-oxo-1,2-cyclobutanedicarboximide, dimethyl acetal; 5-(3methoxy-4-methylphenyl)-3-azabicyclo[3.2.0]heptan-6-one, dimethyl acetal can be prepared from 1-(3-methoxy-4-methylphenyl)-4-oxo-1,2-cyclobutanedicarboximide, dimethyl acetal; 5-(p-methoxyphenyl)-3-azabicycol[3.2.0]heptan-6-one, dimethyl acetal can be prepared from 1-(p-methoxyphenyl)-4oxo-1,2-cyclobutanedicarboximide, dimethyl acetal (m.p. 139°–140° C.); 3-methyl-5-(3',4'-dichlorophenyl)-3-azabicyclo[3.2.0]heptan-6-one, dimethyl acetal can be prepared from N-methyl-1-(3',4'-dichlorophenyl)-4-oxo-1,2-cyclobutanedicarboximide, dimethyl acetal (m.p. 158°–161° C.); 3-methyl-5-(m-trifluoromethylphenyl)-3-azabicyclo[3.2.0]heptan-6-one, dimethyl acetal can be prepared from N-methyl-1-(m-trifluoromethylphenyl)-4-oxo-1,2-cyclobutanecarboximide, dimethyl acetal; and 5-(p-chlorophenyl)-3-azabicyclo[3.2.0]heptan-6-one, dimethyl acetal can be prepared from 1-(p-chlorophenyl)-4-oxo-1,2-cyclobutanedicarboximide, dimethyl acetal (m.p. 143°–144° C.).

EXAMPLE 5

3-Methyl-5-(m-methoxyphenyl)-3-azabicyclo[3.2.0]heptan-6-one, dimethyl acetal free base and fumarate salt A mixture of 5.0 g. of N-methyl-2-(m-methoxyphenyl)maleimide (U.S. Pat. No. 4,131,611), 49.0 g. of dimethoxy ethylene and 0.5 g. of potassium carbonate in 250 ml. of methylene chloride was irradiated in a photochemical reactor fitted with a Pyrex well. After 105 minutes, 5.0 g. of N-methyl-2-(m-methoxyphenyl) maleimide was added and irradiation was resumed. This process was continued until 30 g. of the maleimide had been consumed. The volume of the reaction mixture was reduced to 200 ml., then the mixture was cooled. The solid was removed by filtration and the filtrate was evaporated to 100 ml. and cooled, giving 23.44 g. of 1-(m-methoxyphenyl)-N-methyl-4-oxo-1,2-cyclobutanedicarboximide, 4-dimethyl acetal as a white solid.

base compound as a colorless oil, characterized by $^1$H NMR (CDCl$_3$) δ 7.10–7.45 (m 1H, C-5'), 6.67–7.05 (m, 3H, aromatic), 3.82 (s, 3H, ArOCH$_3$), 3.31 and 2.90 (s, 3H, OCH$_3$), 2.41 (s, 3H, NCH$_3$).

A 1.09 g. portion of this oil was taken up in 10 ml. of acetone and added to a boiling solution of 512 mg. of fumaric acid in 50 ml. of acetone. Cooling and filtration gave 1.47 g. of the desired fumarate salt as a pink solid, m.p. 158°–159° C. Calculated for C$_{16}$H$_{23}$NO$_3$.C$_4$H$_4$O$_4$: C, 61.06; H, 6.92; N, 3.56. Found: C, 61.32; H, 7.12; N, 3.61.

EXAMPLE 6

5-(m-Methoxyphenyl)-3-azabicyclo[3.2.0]heptan-6-one, dimethyl acetal, fumarate To a stirred, cooled solution of 61.5 g. of m-anisidine, 150 ml. of water and 150 ml. of 12 N hydrochloric acid, was added, dropwise during 30 minutes, an aqueous solution composed of 35 g. of sodium nitrite in 80 ml. of water. The temperature was maintained at less than 10° C. The pH was adjusted to 3.0 by the slow addition of 76 g. of sodium bicarbonate. This mixture was filtered and the filtrate slowly added to a stirred and cooled solution of 48.5 g. of maleimide in 400 ml. of acetone containing 12.8 g. of cupric chloride dihydrate. This mixture was stirred and allowed to warm to room temperature. The resulting solid was collected, mixed with 51 g. of 2,6-lutidine and 200 ml. of isopropanol, heated on a steam bath for 0.5 hours and poured into 1500 ml. of water. The resulting solid was collected, partially dissolved in hot ethyl acetate and filtered through an hydrous magnesium silicate. The addition of hexane to the filtrate gave 22 g. of 2-(m-methoxphenyl)maleimide as brown crystals.

A stirred mixture of 5.0 g. of the above maleimide, 25 g. of 1,1-dimethoxy ethylene and 1.0 g. of potassium carbonate in 300 ml. of methylene chloride was irradiated with a Hanovia Ace immersion lamp for 7 hours. The reaction was filtered and the filtrate was concentrated in vacuo, giving a brown tar which was then dissolved in ethyl acetate. The addition of hexane gave a solid which was collected, yielding 4.9 g. of 1-(m- methoxyphenyl)-4-oxo-1,2-cyclobutanedicarboximide-4-dimethyl acetal as a light brown solid.

A stirred mixture of 2.0 g. of the above cyclobutanedicarboximide in 20 ml. of toluene is treated with 20 ml. of Vitride (Reg. TM), dropwise, during 10 minutes, under an atmosphere of nitrogen. The mixture was heated under reflux for 16 hours. The excess hydride was destroyed with 5 N sodium hydroxide and the mixture diluted with water. The toluene phase was separated. The aqueous phase was extracted with methylene chloride. The organic phases were combined, dried, filtered, concentrated and distilled (Kugelrohr) at 0.1 mm., giving 1.4 g. of a brown liquid. A 0.4 g. portion of this liquid was dissolved in acetone and mixed with a solution of 0.176 g. of fumaric acid in 25 ml. of acetone. The resulting solid was crystallized from acetonitrile, giving 108 mg. of the desired product as off-white crystals, m.p. 135°–139° C.

EXAMPLE 7

5-(3-Methoxy-4-methylphenyl)-3-azabicyclo[3.2.0]heptane-6-one, dimethyl acetal

A solution of 2.0 g. of 2-(m-methoxyphenyl)maleimide in 20 ml. of 1,1-dimethoxyethylene was irradiated with a Hanovia Ace immersion lamp for 16 hours as in Example 6, but in the absence of potassium carbonate. Evaporation of volatile material gave a black tar which one being purified by high performance liquid chromatography with a 40:60 ethyl acetate-hexane eluate gave 0.96 g. of tan crystals, m.p. 125°–135° C. Recrystallization from ethyl acetate-hexane gave 0.38 g. of 1-(3-methoxy-4-methylphenyl)-4-oxo-1,2-cyclobutanedicarboximide, dimethyl acetal, m.p. 148°–150° C., characterized by $^1$H NMR (CDCl$_3$) 7.62, 7.06, 6.87 (d, 3H, aromatic), 3.92, 3.42, and 3.06 (s, 3H, OCH$_3$), 2.77 (s, 3H, aryl-CH$_3$).

Reduction of this imide as in Example 6 gave 5(3-methoxy-4-methylphenyl)-3-azabicyclo[3.2.0]heptane-6-one, dimethyl acetal.

EXAMPLE 8

3-Allyl-5-(m-methoxyphenyl)-3-azabicyclo[3.2.0]heptan-6-one, dimethyl acetal

A 3.5 g. portion of 1-(m-methoxyphenyl)-4-oxo-1,2-cyclobutanedicarboximide-4-dimethyl acetal was converted to 5-(m-methoxyphenyl)-3-azabicyclo[3.2.0]heptan-6-one, dimethyl acetal as described in Example 1. The resulting brown liquid was distilled in a Kugelrohr apparatus at 180° C. and 0.2 mm. A 0.8 g. portion of the resulting oil was combined with 0.6 g. of sodium carbonate, 0.5 g. of allyl bromide and 30 ml. of toluene and stirred overnight. The mixture was filtered, the filtrate washed with ethyl acetate and concentrated to an oil. This oil is distilled in a Kugelrohr apparatus, at 0.1 mm., giving 0.223 g. of the desired product as a yellow liquid, b.p. 130° C., characterized by $^1$H NMR (CDCl$_3$) δ 7.22 and 6.80 (m, 4H, aromatic), 5.96 and 5.16 (m, 3H, vinyl), 3.83 (s, 3H, aryl-OCH$_3$).

EXAMPLE 9

3-Cyclopropylmethyl-5-(m-methoxyphenyl)-3-azabicyclo[3.2.0]heptan-6-one, dimethyl acetal In the manner of Example 8, 5-(m-methoxyphenyl)-3-azabicyclo[3.2.0]heptan-6-one, dimethyl acetal, can be reacted with cyclopropylmethyl bromide and sodium carbonate in toluene to give 3-cyclopropylmethyl-5-(m-methoxyphenyl)-3-azabicyclo[3.2.0]heptan-6-one, dimethyl acetal.

EXAMPLE 10

3-Phenethyl-5-(m-methoxyphenyl)-3-azabicyclo[3.2.0]heptan-6-one, dimethyl acetal In the manner of Example 9, 5-(m-methoxyphenyl)-3-azabicyclo[3.2.0]heptan-6-one, dimethyl acetal can be reacted with 1-bromo-2-phenylethane and sodium carbonate in toluene to give 3-phenethyl-5-(m-methoxyphenyl)-3-azabicyclo[3.2.0]heptan-6-one, dimethyl acetal.

EXAMPLE 11

3-Methyl-5-(m-hydroxyphenyl)-3-azabicyclo[3.2.0]heptan-6-one, dimethyl acetal

To 2.4 g. of 50% sodium hydride in mineral oil in 15 ml. of dimethylformamide, chilled in ice, was added a solution of 4.4 ml. of ethanethiol in 10 ml. of dimethylformamide over 30 minutes. The mixture was stirred for 15 minutes, then a solution of 2.77 g. of 3-methyl-5-(m-methoxyphenyl)-3-azabicyclo[3.2.0]heptan-6-one, dimethyl acetal in 10 ml. of dimethylformamide was added. The mixture was refluxed for 3 hours, the dimethylformamide was evaporated at reduced pressure, 25 ml. of water was added and the mixture was extracted twice with ether. Charcoal was added to the combined ether extracts, the mixture was filtered and glacial acetic acid was added to pH 8. The solid was collected and recrystallized from ethyl acetate-methanol, giving 1.0 g. of the desired product as colorless crystals, m.p. 188°–191° C. Calculated for C$_{15}$H$_{21}$NO$_3$: C, 68.42; H, 8.04; N, 5.32. Found: C, 68.70; H, 7.83; N, 5.28.

EXAMPLE 12

3-Methyl-5-(m-methoxyphenyl)-3-azabicyclo[3.2.0]heptan-6-one

A mixture of 4.99 g. of 3-methyl-5-(m-methoxyphenyl)-3-azabicyclo[3.2.0]heptan-6-one, dimethyl acetal and 50 ml. of 10% hydrochloric acid was heated at reflux for 15 minutes, cooled, diluted with 50 ml. of 10% aqueous sodium hydroxide and worked up with dichloromethane, giving a red oil which was distilled in a Kugelrohr apparatus at 140° C./0.15 mm., giving 3.39 g. of the product as a pale yellow liquid, characterized by IR(film) 2951 (CH$_2$), 2786 (NCH$_3$), 1707 (CO) cm$^{-1}$; $^1$H NMR (CDCl$_3$) δ 7.24 (t, J=10 Hz, 1H, C-5'), 6.68–7.04 (m, 3H, aromatic), 3.80 (s, 3H, OCH$_3$), 2.36 (s, 3H, NCH$_3$). Calc'd. for C$_{14}$H$_{17}$NO$_2$: C, 72.70; H, 7.41; N, 6.06. Found: C, 71.84; H, 7.62; N, 5.98.

EXAMPLE 13

5-(m-Methoxyphenyl)-3,5',5'-trimethyl-spiro[3-azabicyclo[3.2.0]heptane-6,2'-[1,3]dioxane]

A mixture of 1.18 g. of 3-methyl-5-(m-methoxyphenyl)-3-azabicyclo[3.2.0]heptan-6-one, 0.78 g. of 2,2-dimethyl-1,3-propanediol and 1.05 g. of p-toluenesulfonic acid in 25 ml. of toluene was heated at reflux under a Dean-Stark trap for 29 hours. The mixture was cooled, diluted with ether, washed with 10% sodium hydroxide, and then with water giving a brown oil. This oil was distilled in a Kugelrohr apparatus at 175° C. and 0.10 mm., giving the desired product as a colorless oil.

By the above procedure, using ethylene glycol, there was obtained 3-methyl-5-(m-methoxyphenyl)-spiro-[3- azabicyclo[3.2.0]heptane-6,2'-[1,3]dioxalane]fumarate, m.p. 132°–135° C. Calculated for $C_{23}H_{31}NO_2$: C, 63.73; H, 7.21; N, 3.23. Found: C, 64.18; H, 7.23; N, 3.27.

Having thus described the invention, what is claimed is:

1. Compounds having the formula:

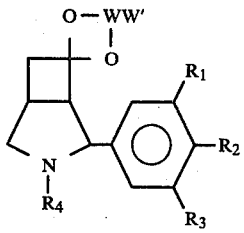

wherein $R_1$, $R_2$ and $R_3$ are each individually selected from the class consisting of hydrogen, hydroxy, chloro, bromo, $C_1$-$C_3$ alkyl, $C_1$-$C_3$ alkoxy, and trifluoromethyl, and any two or more of $R_1$, $R_2$ and $R_3$ may be the same; $R_4$ is selected from the group consisting of hydrogen, $C_1$-$C_3$ alkyl, $C_1$-$C_4$ alkyl, cyclopropylmethyl and phenethyl; and W and W' each represent a monovalent alkyl moiety having up to 3 carbon atoms or W-W' jointly represent a divalent moiety of the formula:

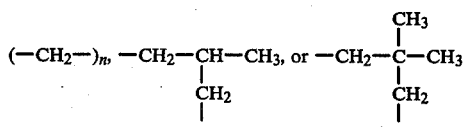

wherein n is an integer of 2 or 3; and the non-toxic pharmacologically-acceptable acid-addition salts thereof.

2. A compound according to claim 1 which is 3-methyl-5-phenyl-3-azabicyclo[3.2.0]heptan-6-one, dimethyl acetal.

3. A compound according to claim 1 which is 3-methyl-5-phenyl-3-azabicyclo[3.2.0]heptan-6-one, dimethyl acetal, fumarate.

4. A compound according to claim 1 which is 3-methyl-5-(m-methoxyphenyl)-3-azabicyclo[3.2.0]heptan-6-one, dimethyl acetal.

5. A compound according to claim 1 which is 3-methyl-5-(m-methoxyphenyl)-3-azabicyclo[3.2.0]heptan-6-one, dimethyl acetal, fumarate.

6. A compound according to claim 1 which is 5-(m-methoxyphenyl)-3-azabicyclo[3.2.0]heptan-6-one, dimethyl acetal, fumarate.

7. A compound according to claim 1 which is 3-allyl-5-(m-methoxyphenyl)-3-azabicyclo[3.2.0]heptan-6-one, dimethyl acetal.

8. A compound according to claim 1 which is 3-methyl-5-(m-hydroxyphenyl)-3-azabicyclo[3.2.0]heptan-6-one, dimethyl acetal.

9. A compound according to claim 1 which is 5-(m-methoxyphenyl)-3,5',5'-trimethyl-spiro[3-azabicyclo[3.2.0]heptane-6,2'-[1,3]dioxane].

10. A method of treating pain in a mammal, which method comprises administering to said mammal a therapeutically effective amount of a compound having a formula:

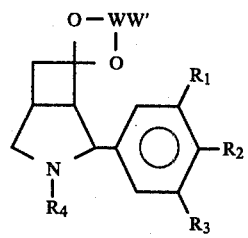

wherein $R_1$, $R_2$ and $R_3$ are each individually selected from the class consisting of hydrogen, hydroxy, chloro, bromo, $C_1$-$C_3$ alkyl, trifluoromethyl and any two or more of $R_1$, $R_2$ and $R_3$ may be the same; $R_4$ is selected from the class consisting of hydrogen, $C_1$-$C_3$ alkyl, $C_1$-$C_4$ alkyl, cyclopropolmethyl and phenethyl; and W and W' each represent a monovalent alkyl moiety having up to three carbon atoms or W-W' jointly represent a divalent moiety of the formula:

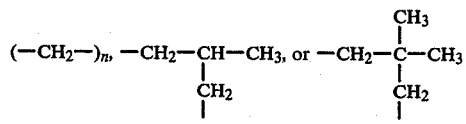

wherein n is an integer of two or three; and the non-toxic pharmacologically-acceptable acid-addition salts thereof.

11. A method according to claim 10, wherein the compound is 3-methyl-5-phenyl-3-azabicyclo[3.2.0]heptan-6-one, dimethyl acetal.

12. A method according to claim 10, wherein the compound is 3-methyl-5-phenyl-3-azabicyclo[3.2.0]heptan-6-one, dimethyl acetal, fumarate.

13. A method according to claim 10, wherein the compound is 3-methyl-5-(m-methoxyphenyl)-3-azabicyclo[3.2.0]heptan-6-one, dimethyl acetal.

14. A method according to claim 10, wherein the compound is 3-methyl-5-(m-methoxyphenyl)-3-azabicyclo[3.2.0]heptan-6-one, dimethyl acetal, fumarate.

15. A method according to claim 10, wherein the compound is 5-(m-methoxyphenyl)-3-azabicyclo[3.2.0]heptan-6-one, dimethyl acetal, fumarate.

16. A method according to claim 10, wherein the compound is 3-allyl-5-(m-methoxyphenyl)-3-azabicyclo[3.2.0]heptan-6-one, dimethyl acetal.

17. A method according to claim 10, wherein the compound is 3-methyl-5-(m-hydroxyphenyl)-3-azabicyclo[3.2.0]heptan-6-one, dimethyl acetal.

18. A method according to claim 10, wherein the compound is 5-(m-methoxyphenyl)-3,5',5'-trimethyl-spiro-[3-azabicyclo[3.2.0]heptane-6,2'[1,3]dioxane].

19. The compounds of claim 1 wherein $R_2$ or $R_3$ is alkoxy and the other is hydrogen, and $R_1$ is hydrogen.

20. The compounds of claim 19 in which $R_2$ or $R_3$ is methoxy.

21. The compounds of claim 1 wherein $R_4$ is a lower alkyl.

22. The compounds of claim 21 in which $R_4$ is methyl.

23. The compounds of claim 1 wherein $R_2$ or $R_3$ is alkoxy and the other is hydrogen, $R_1$ is hydrogen, and $R_4$ is lower alkyl.

24. The compounds of claim 23 in which $R_2$ or $R_3$ is methoxy and $R_4$ is methyl.

* * * * *